United States Patent [19]

Speranza et al.

[11] Patent Number: 4,681,965

[45] Date of Patent: Jul. 21, 1987

[54] PHOSPHORUS CONTAINING AROMATIC AMINO POLYOLS

[75] Inventors: George P. Speranza; Michael E. Brennan, both of Austin; Robert A. Grigsby, Jr., Georgetown, all of Tex.

[73] Assignee: Texaco Inc., White Plains, N.Y.

[21] Appl. No.: 763,503

[22] Filed: Aug. 8, 1985

[51] Int. Cl.$^4$ .............................................. C07F 9/40
[52] U.S. Cl. ..................................... 558/162; 558/135
[58] Field of Search ................................ 558/135, 162

[56] References Cited

U.S. PATENT DOCUMENTS

| | | | |
|---|---|---|---|
| 2,635,112 | 4/1953 | Fields | 558/169 |
| 3,076,010 | 1/1963 | Beck et al. | 558/169 |
| 4,052,487 | 10/1977 | Sturtz et al. | 558/169 |
| 4,310,592 | 1/1982 | Schmitz | 564/390 |

*Primary Examiner*—Anton H. Sutto
*Attorney, Agent, or Firm*—Jack H. Park; Kenneth R. Priem

[57] ABSTRACT

A class of Mannich condensates containing phosphorus prepared by reacting a phenol with formaldehyde and a primay amine, and then reacting the product with formaldehyde and a dialkyl phosphite. Useful applications include use as a fire retardant additive in polyurethane foams.

7 Claims, No Drawings

PHOSPHORUS CONTAINING AROMATIC AMINO POLYOLS

FIELD OF THE INVENTION

This invention pertains to the introduction of phosphorus into aromatic amino polyols by the Mannich reaction and its use as a fire retardant additive in polyurethane foams.

DESCRIPTION OF THE RELATED ART

The Mannich reaction involves the reaction of an acidic hydrogen with formaldehyde and an amino base. U.S. Pat. No. 4,310,592 to Schmitz illustrates the manner in which the Mannich reaction can be used to prepare useful products. The patent teaches that when an aliphatic amine and formaldehyde are reacted with phenol, the reaction yields predominantly an ortho substituted Mannich base. According to the patent, the reaction proceeds by the following general equation:

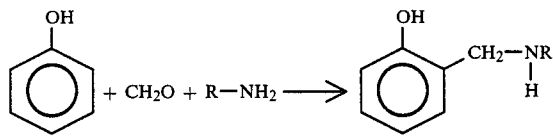

wherein R is an alkyl radical containing from about 12 to 22 carbon atoms.

U.S. Pat. No. 3,076,010 discloses that when instead of a phenol, a dialkyl phosphite is reacted with an aldehyde or ketone and a dialkanolamine, a compound is formed which may be represented by the formula:

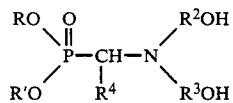

in which R and R' may be the same or different alkyl or haloalkyl radicals, $R^2$ and $R^3$ may be the same or different lower alkylene radicals and $R_4$ is hydrogen or an alkyl radical. U.S. Pat. No. 3,076,010 instructs that these compounds may be made according to the general reaction:

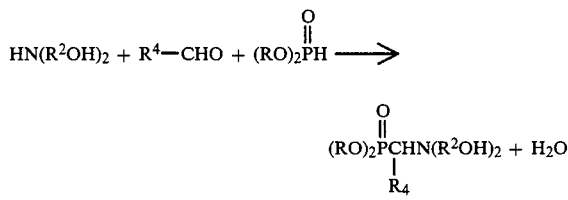

wherein R, R', $R^2$, $R^3$ and $R^4$ are defined as above.

U.S. Pat. No. 4,052,487 represents an improvement on the teachings of U.S. Pat. No. 3,076,010 by disclosing the development of a diol phosphonate having the general formula:

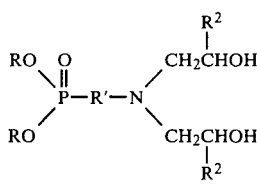

in which R is an alkyl group with 1 to 4 carbon atoms, $R^2$ is hydrogen, a methyl or an ethyl group, and R' is $-CH_2-CH_2-CH_2-$ or

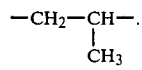

This diol-phosphonate was found useful as a flameproofing additive in polyurethane foams.

The invention disclosed herein combines elements of the two reactions disclosed in U.S. Pat. Nos. 4,310,592 and 3,076,010 to produce a new class of Mannich condensates.

SUMMARY OF THE INVENTION

The invention is a compound comprising a phenol which is substituted by a phosphorus containing structure having the formula:

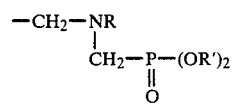

in which R is hydrogen, an alkyl, alkanol or polyoxyalkylene group, and R' is an alkyl group.

DESCRIPTION OF THE PREFERRED EMBODIMENTS

The Mannich reaction involves the reaction of an acidic hydrogen with formaldehyde and an amino base. The phosphorus-hydrogen bond is acidic in dialkyl phosphites and will undergo the Mannich reaction with an N—H bond in the presence of formaldehyde. When phosphorus is introduced into aromatic amino polyols by the Mannich reaction, the resulting products have a variety of uses; for example, fire retardants for rigid urethane foams and epoxy plastics, lubricating additives, gasoline wear-inhibiting additives, corrosion inhibitors and surfactants, and may also be propoxylated to other useful polyols for urethanes.

These compounds may be prepared by a Mannich reaction between a phenol, formaldehyde, a primary amine and a dialkyl phosphite as illustrated by the following reaction sequence:

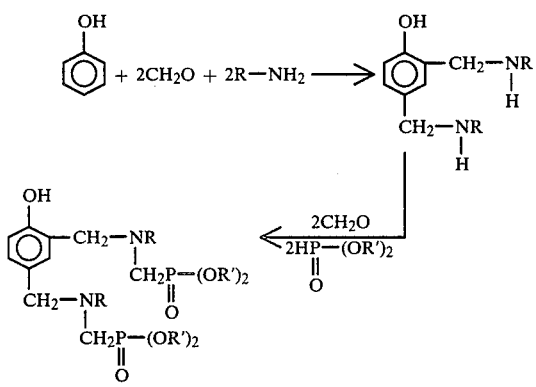

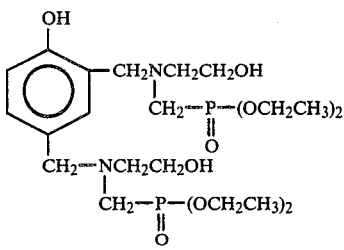

in which R is hydrogen, an alkyl, alkanol or polyoxyalkylene group, and R' is an alkyl group. It is preferred that R is an alkanol group. Especially preferred is —CH₂—CH₂OH. A preferred compound may be represented by the following structure:

OH
⌬—CH₂NCH₂CH₂OH
  |
  CH₂—P—(OCH₂CH₃)₂
       ‖
       O
—CH₂—NCH₂CH₂OH
  |
  CH₂—P—(OCH₂CH₃)₂
       ‖
       O

Some useful phenols include phenol, nonylphenol, isopropylphenol, cresol, dodecylphenol or Bisphenol A. It is preferred that the phosphite used be dimethyl phosphite or diethyl phosphite.

The conditions within which this invention is useful include a temperature range of 15° to 150° C. and a pressure range of 1 to 200 atmospheres. It is preferred that the reaction be run at a pressure of 1 atmosphere.

Though the products of this invention have a number of applications, of particular interest is their application as fire retarding agents for plastics. Those products which contain several hydroxy groups are especially suitable as fire retardants for urethane foams. This invention and its application as a fire retardant for urethane foams will be further illustrated by the following non-limiting examples.

EXAMPLE 1

To a 1 liter, three-necked flask equipped with a stirrer, thermometer and dropping funnel were added 220 g of nonylphenol (1.0 moles) and 61 g of monoethanolamine. The mixture was cooled to 15° C. and 81.1 g of formalin (1.0 moles) were added slowly while keeping the temperature at 15°–20° C. After all the formalin was added, the mixture was stirred for 30 minutes and then heated to 90° C. and held at this temperature under about 20 mm pressure for two hours. The product weighed 291.5 g and analysis indicated 50% of ortho hydrogens on nonylphenol underwent the Mannich reaction.

To 100 g of the product described above was added 47.13 g of diethyl phosphite (0.341 moles). Then 27.65 g of formalin (0.341 moles) was added and the temperature allowed to rise to 55° C. The contents were heated to 90° C. and held at 90°–108° C. for five hours at full water aspirator reduced pressure while removing water. The final product weighed 142.2 g and was a thick, light brown liquid. It had a hydroxyl number of 78 and a total amine content of 1.85 meq/g.

The procedure described above illustrates in general the technique used in this work. Specific examples are described in Tables I and II using nonylphenol, phenol and Bisphenol A. A wide variety of amines were used. Diethyl phosphite was used in all runs shown except 11 of Table I in which dimethyl phosphite was used.

TABLE I

REACTIONS OF DIETHYL PHOSPHITE, AMINES, FORMALDEHYDE AND NONYLPHENOL

| Ex. | Nonylphenol, Moles | Amines, Moles | CH₂O, Moles | DEP, Moles | Analysis Total Amine | Analysis Hydroxyl Number | Reaction Stage #1 Hrs-Temp., °C. | Reaction Stage #2 Hrs-Temp., °C. |
|---|---|---|---|---|---|---|---|---|
| 1 | 0.34 | MEA 0.34 | 0.34 | 0.34 | 1.85 | 78 | 2  110 | 5  100 |
| 2 | 0.52 | DGA 0.5 | 0.50 | 0.5 | 1.81 | 236 | 1  110 | 4  110 |
| 3 | 0.14 | M-600 0.28 | 0.28 | 0.28 | 1.12 | 57 | — | 3  100 |
| 4 | 0.07 | M-1000 0.13 | 0.13 | 0.13 | 0.56 | 23 | — | 3  110 |
| 5 | 0.17 | M-300 0.33 | 0.33 | 0.33 | 1.62 | 34 | 3  110 | 3  110 |
| 6 | 0.25 | D-400 0.5 | 0.50 | 0.50 | 2.49 | 150 | 4  110 | 4  110 |
| 7 | 0.25 | D-400 0.5 | 0.50 | 0.50 | 2.14 | 119 | 4  110 | 4  110 |
| 8 | 0.25 | ED-600 0.5 | 0.50 | 0.50 | 2.01 | 123 | 8  110 | 4  110 |
| 9 | 0.07 | T₃EDMA 0.13 | 0.13 | 0.13 | 2.30 | 207 | 3  110 | 4  110 |
| 10 | 0.1 | T₄EGMA 0.20 | 0.20 | 0.20 | 5.22 | 192 | 3  110 | 3  110 |
| 11 | 0.14 | M-600 0.28 | 0.28 | DMP 0.28 | 1.05 | 61 | 2  110 | 2  110 |
| 12 | 0.5 | DGA 1.0 | 0.93 | 0.93 | 2.50 | 200 | 3  110 | 3  110 |
| 13 | 0.5 | MEA 1.0 | 0.92 | 0.92 | 2.23 | 169 | 3  110 | 3  110 |
| 14 | 0.5 | M-360 | 0.97 | 0.97 | 1.36 | 80 | 3  110 | 3  110 |

TABLE I-continued

REACTIONS OF DIETHYL PHOSPHITE, AMINES,
FORMALDEHYDE AND NONYLPHENOL

| Ex. | Nonyl-phenol, Moles | Amines, Moles | $CH_2O$, Moles | DEP, Moles | Analysis Total Amine | Analysis Hydroxyl Number | Reaction Stage #1 Hrs-Temp., °C. | Reaction Stage #2 Hrs-Temp., °C. |
|---|---|---|---|---|---|---|---|---|
| | 1.0 | | | | | | | |

Monoethanolamine (MEA) = $NH_2CH_2CH_2OH$
DIGLYCOLAMINE ® Agent = $NH_2CH_2CH_2OCH_2CH_2OH$ JEFFAMINE ® M-600 = $CH_3-O-CH_2CH_2\left(O-CH_2-\underset{\underset{CH_3}{|}}{CH}\right)_9 NH_2$ JEFFAMINE ® M-1000 = $CH_3O[CH_2CH_2O]_{18.5}\left(CH_2-\underset{\underset{CH_3}{|}}{CH}-O\right)_{1.6}-CH_2\underset{\underset{CH_3}{|}}{CH}NH_2$ JEFFAMINE ® M-300 = $CH_3(CH_2)_{9-11}OCH_2-\underset{\underset{CH_3}{|}}{CH}-OCH_2\underset{\underset{CH_3}{|}}{CH}-NH_2$ JEFFAMINE ® D-400 = $NH_2-(\underset{\underset{CH_3}{|}}{CH}-CH_2O)_6-CH_2-\underset{\underset{CH_3}{|}}{CH}-NH_2$ JEFFAMINE ® ED-600 = $O-[(CH_2CH_2O)_{4.35}-(CH_2-\underset{\underset{CH_3}{|}}{CH}-O)_{0.75}-(CH_2-\underset{\underset{CH_3}{|}}{CH}-NH_2)]_2$ $T_3EGMA = NH_2-(CH_2CH_2O)_3H$
$T_4EGMA = NH_2-(CH_2CH_2O)_4H$
JEFFAMINE ® M-360 = $CH_3CH_2CH_2CH_2O(CH_2CH_2O)_4-CH_2-\underset{\underset{CH_3}{|}}{CH}-OCH_2-\underset{\underset{CH_3}{|}}{CH}-NH_2$ All amines obtained from Texaco Chemical Company.

TABLE II

REACTIONS OF DIETHYL PHOSPHITE, AMINES,
FORMALDEHYDE AND PHENOL

| Ex. | Phenol, Moles | Amines, Moles | $CH_2O$, Moles | DEP, Moles | Analysis Total Amine | Analysis Hydroxyl Number | Reaction Stage #1 Hrs-Temp., °C. | Reaction Stage #2 Hrs-Temp., °C. |
|---|---|---|---|---|---|---|---|---|
| 1 | 1.0 | M-300 0.33 | 0.33 | 0.33 | 1.86 | 105 | 3 110 | 5 110 |
| 2 | 0.5 | M-300 1.0 | 1.0 | 1.0 | 2.0 | 128 | 3 110 | 5 110 |
| 3 | 0.5 | M-1000 0.5 | 0.5 | 0.5 | 0.75 | 48 | 4 110 | 5 110 |
| 4 | 0.5 | M-600 1.0 | 1.0 | 1.0 | 1.18 | 83 | 4 110 | 4 110 |
| 5 | 1.0 | M-600 1.0 | 1.0 | 1.0 | 1.17 | 83 | 3 110 | 4 110 |
| 6 | 0.25 | M-1000 0.5 | 0.5 | 0.5 | 0.71 | 36 | 9 110 | 6 110 |
| 7 | 0.25 | ED-600 0.5 | 0.5 | 0.5 | 2.13 | 132 | 8 110 | 5 110 |
| 8 | 0.5 | MEA 1.5 | 1.5 | 1.5 | 3.15 | 176 | 3 110 | 3 110 |
| 9 | 0.25 | D-400 0.5 | 0.46 | 0.46 | 2.78 | 171 | 3 110 | 4 110 |

TABLE III

REACTIONS OF DIETHYL PHOSPHITE, AMINES,
FORMALDEHYDE AND BISPHENOL A

| Ex. | BPA, Moles | Amines, Moles | $CH_2O$, Moles | DEP, Moles | Analysis Total Amine | Analysis Hydroxyl Number | Reaction Stage #1 Hrs-Temp., °C. | Reaction Stage #2 Hrs-Temp., °C. |
|---|---|---|---|---|---|---|---|---|
| 1 | 0.16 | M-300 0.33 | 0.33 | 0.33 | 1.85 | 30 | 3 110 | 3 110 |
| 2 | 0.17 | M-600 0.33 | 0.33 | 0.33 | 1.14 | 80 | 3 110 | 3 110 |
| 3 | 0.25 | ED-600 0.5 | 0.5 | 0.5 | — | — | 5 110 | Polymer |
| 4 | 0.03 | M-1000 0.03 | 0.06 | 0.06 | — | — | 3 110 | Liquid 50° C. |

TABLE III-continued
REACTIONS OF DIETHYL PHOSPHITE, AMINES, FORMALDEHYDE AND BISPHENOL A

| Ex. | BPA, Moles | Amines, Moles | CH$_2$O, Moles | DEP, Moles | Analysis Total Amine | Analysis Hydroxyl Number | Reaction Stage #1 Hrs-Temp., °C. | Reaction Stage #2 Hrs-Temp., °C. |
|---|---|---|---|---|---|---|---|---|
| | | M-300 (0.03) | | | | | | |

EXAMPLE 2

Several of the products prepared in this invention were tested in rigid polyurethane and polyurethane-isocyanurate foam formulations. The foams were prepared by standard one-shot, free-rise techniques. Formulation components were mixed at 2700 rpm and poured into an 8"×8"×12" (600 g pour) open mold and allowed to rise. The resulting foams were allowed to stand at ambient conditions for at least three days before determination of physical properties.

It was found that the use of the products of this invention adds fire retardant properties to the foams, improves both insulation values (K-factor) and compression strength, and results in higher heat distortion temperatures. The improvement of foam physical properties also occurs in isocyanurate foams, and, in addition, the friability of the foams is improved. It was found that foams made using DIGLYCOLAMINE® (DGA) agent were easiest to work with and were conveniently prepared.

Formulations, reaction profiles and foam physical properties are detailed in the following table for various comparative and inventive examples.

EXPERIMENTAL FIRE RETARDANT EVALUATIONS

| Fire Retardant | Comparative Examples | | | | | Nonylphenol/MEA Based (See Table I) | | | Nonylphenol/DGA Based (See Table I) | |
|---|---|---|---|---|---|---|---|---|---|---|
| | — | AB-80[1] | — | AB-80 | AB-80 | Ex. 1 | Ex. 13 | Ex. 13 | Ex. 2 | Ex. 2 |
| Formulation, pbw | | | | | | | | | | |
| THANOL® R-350-X[2] (OH = 526) | 37.3 | 35.1 | 24.6 | 23.2 | — | 34.7 | 34.3 | 22.7 | 34.0 | 22.5 |
| TERATE® 203[3] (OH = 309) | — | — | 16.4 | 15.4 | — | — | — | 15.0 | — | 14.9 |
| R-440[4] (OH = 258) | — | — | — | — | — | — | — | — | — | — |
| R-440[4] (OH = 252) | — | — | — | — | 28.9 | — | — | — | — | — |
| Fire Retardant | — | 5.0 | — | 5.0 | 5.0 | 5.0 | 4.9 | 4.9 | 4.8 | 4.8 |
| DC-193[5] | 0.5 | 0.5 | 0.5 | 0.5 | 0.5 | 0.5 | 0.5 | 0.5 | 0.5 | 0.5 |
| R-11A[6] | 13.0 | 13.0 | 13.0 | 13.0 | 12.0 | 13.0 | 13.0 | 13.0 | 13.0 | 13.0 |
| Water | — | — | 0.3 | 0.3 | — | — | — | 0.3 | — | 0.3 |
| FOMREZ® UL-32[7] | — | — | 0.01 | 0.01 | — | — | — | 0.01 | — | 0.01 |
| T-45[8] | — | — | — | — | 1.5 | — | — | — | — | — |
| MONDUR® MR[9] | 49.2 | 46.4 | 45.2 | 42.6 | 52.1 | — | — | — | — | — |
| PAPI® 27[10] | — | — | — | — | — | 46.8 | 47.3 | 43.6 | 47.7 | 44.0 |
| Index | 1.05 | 1.05 | 1.05 | 1.05 | 3.0 | 1.05 | 1.05 | 1.05 | 1.05 | 1.05 |
| Reaction Profile | | | | | | | | | | |
| Times (sec), mixing | 15 | 15 | 12 | 12 | 3 | 15 | 15 | 12 | 15 | 12 |
| Times (sec), cream | 25 | 24 | 17 | 20 | 8 | 28 | 28 | 21 | 25 | 21 |
| Times (sec), gel | 78 | 86 | 52 | 70 | 21 | 99 | 98 | 71 | 92 | 73 |
| Times (sec), tack free | 106 | 110 | 81 | 94 | 32 | 117 | 124 | 113 | 108 | 102 |
| Times (sec), rise | 187 | 186 | 139 | 153 | 64 | 199 | 210 | 180 | 251 | 198 |
| Initial Surface Friability | None | None | Yes | None | Yes | None | None | Yes | None | None |
| Foam appearance | Good | Good | Fair | Good | Good | Good | Good | Good | Good | Good |
| Physical Properties | | | | | | | | | | |
| Density, pcf | 1.96 | 1.99 | 1.65 | 1.72 | 1.86 | 1.85 | 1.92 | 1.63 | 1.97 | 1.68 |
| K-factor | 0.118 | 0.119 | 0.112 | 0.128 | 0.117 | 0.111 | 0.115 | 0.112 | 0.111 | 0.112 |
| Compressive strength, | | | | | | | | | | |
| psi, with rise | 47.57 | 41.92 | 40.81 | 38.31 | 38.41 | 46.89 | 48.61 | 37.39 | 41.79 | 31.66 |
| against rise | 16.58 | 14.90 | 10.54 | 10.51 | 11.05 | 15.82 | 14.89 | 10.15 | 12.52 | 7.36 |
| Heat distortion, °C. | 158 | 144 | 136 | 115 | 191 | 137 | 142 | 131 | 154 | 136 |
| Closed cells, % | 92.25 | 91.51 | 92.55 | 91.43 | 91.30 | 91.10 | 93.07 | 92.21 | 92.59 | 92.94 |
| Friability, % wt. loss, 10 min | 6.63 | 5.88 | 2.07 | 2.43 | 24.90 | 5.64 | 7.62 | 4.93 | 6.27 | 3.73 |
| ASTM 1692 Burn, in/min (BHA) | 2.57 | 1.64 | 2.27 | 1.82 | 1.19 | 3.07 | 2.06 | 2.86 | 1.86 | 1.76 |
| Butler Chimney Test | | | | | | | | | | |
| Flame height, in. | >11 | >11 | >11 | >11 | 4.33 | >11 | >11 | >11 | >11 | >11 |
| Sec. to extinguish | 26 | 20 | 25 | 14 | 12.33 | 24 | 19 | 17 | 23 | 16 |
| % wt. retained | 20.1 | 64.3 | 31.4 | 68.7 | 93.2 | 36.2 | 52.0 | 54.7 | 43.3 | 58.0 |
| Dimensional Stability | | | | | | | | | | |
| 158° F., 100% R-H | | | | | | | | | | |
| 1 week ΔV | +2.7 | +8.4 | +2.9 | +16.5 | +5.3 | +2.9 | +3.2 | +4.1 | +4.3 | +4.1 |
| ΔW | −0.3 | −0.7 | −0.6 | −1.0 | −1.9 | +0.3 | +0.2 | +0.1 | −0.4 | −0.6 |
| ΔL | +1.8 | +5.4 | +2.2 | +11.9 | +3.4 | +2.5 | +2.2 | +3.3 | +2.5 | +2.4 |
| 4 weeks ΔV | +5.4 | +16.8 | +7.7 | +42.5 | +9.8 | +5.4 | +6.1 | +7.7 | +8.4 | +10.3 |

-continued
EXPERIMENTAL FIRE RETARDANT EVALUATIONS

| | | | | | | | | | |
|---|---|---|---|---|---|---|---|---|---|
| ΔW | −0.3 | −1.2 | −0.6 | −2.8 | −3.1 | +0.4 | +0.2 | 0.0 | 0.0 | −0.1 |
| ΔL | +3.4 | +9.9 | +5.1 | +23.0 | +5.9 | +4.6 | +4.0 | +5.7 | +5.0 | +5.9 |

| | Nonylphenol/DGA Based (See Table I) | | | Nonylphenol/M-300 Based (See Table I) | | | Bispenol A/M-300 Based (See Table II) | | |
|---|---|---|---|---|---|---|---|---|---|
| Fire Retardant | Ex. 12 | Ex. 12 | Ex 12 | Ex. 5 | Ex. 5 | Ex. 5 | Ex. 1 | Ex. 1 | Ex. 1 |
| Formulation, pbw | | | | | | | | | |
| THANOL ® R-350-X² (OH = 526) | 34.1 | 22.5 | — | 34.9 | 23.1 | — | 35.0 | 23.1 | — |
| TERATE ® 203³ (OH = 309) | — | 15.0 | — | — | 15.3 | — | — | 15.3 | — |
| R-440⁴ (OH = 258) | — | — | 26.4 | — | — | 28.2 | — | — | 28.3 |
| R-440⁴ (OH = 252) | | | | | | | | | |
| Fire Retardant | 4.9 | 4.9 | 4.6 | 5.0 | 5.0 | 4.9 | 5.0 | 5.0 | 4.9 |
| DC-193⁵ | 0.5 | 0.5 | 0.5 | 0.5 | 0.5 | 0.5 | 0.5 | 0.5 | 0.5 |
| R-11A⁶ | 13.0 | 13.0 | 12.0 | 13.0 | 13.0 | 12.0 | 13.0 | 13.0 | 12.0 |
| Water | — | 0.3 | — | — | 0.3 | — | — | 0.3 | — |
| FOMREZ ® UL-32⁷ | — | 0.01 | — | — | 0.01 | — | — | 0.01 | — |
| T-45⁸ | — | — | 1.0 | — | — | 1.0 | — | — | 1.0 |
| MONDUR ® MR⁹ | | | | | | | | | |
| PAPI ® 27¹⁰ | 47.5 | 43.8 | 55.5 | 46.6 | 42.8 | 53.4 | 46.5 | 42.8 | 53.3 |
| Index | 1.05 | 1.05 | 3.0 | 1.05 | 1.05 | 3.0 | 1.05 | 1.05 | 3.0 |
| Reaction Profile | | | | | | | | | |
| Times (sec), mixing | 15 | 12 | 6 | 15 | 12 | 6 | 15 | 12 | 6 |
| Times (sec), cream | 27 | 21 | 14 | 25 | 17 | 13 | 26 | 17 | 15 |
| Times (sec), gel | 92 | 71 | 46 | 97 | 69 | 49 | 97 | 65 | 49 |
| Times (sec), tack free | 112 | 91 | 56 | 128 | 95 | 93 | 123 | 99 | 77 |
| Times (sec), rise | 223 | 202 | 134 | 211 | 165 | 152 | 219 | 166 | 156 |
| Initial Surface Friability | None | None | None | None | None | Yes | None | None | Yes |
| Foam appearance | Good | Good | Good | Good | Good | Good | Good | Good | Good |
| Physical Properties | | | | | | | | | |
| Density, pcf | 1.97 | 1.70 | 1.84 | 2.01 | 1.68 | 1.96 | 2.00 | 1.68 | 1.99 |
| K-factor | 0.114 | 0.110 | 0.110 | 0.121 | 0.118 | 0.122 | 0.118 | 0.117 | 0.119 |
| Compressive strength, | | | | | | | | | |
| psi, with rise | 43.80 | 34.47 | 33.12 | 41.46 | 30.69 | 35.03 | 44.26 | 35.26 | 40.64 |
| against rise | 12.52 | 8.25 | 9.64 | 14.93 | 10.33 | 13.68 | 15.18 | 10.59 | 15.27 |
| Heat distortion, °C. | 145 | 127 | 207 | 144 | 124 | 212 | 153 | 123 | 204 |
| Closed cells, | 93.24 | 93.22 | 93.17 | 92.14 | 93.10 | 92.67 | 92.10 | 93.27 | 91.88 |
| Friability, % wt. loss, 10 min | 5.38 | 4.24 | 4.46 | 5.79 | 2.32 | 6.42 | 7.43 | 2.30 | 11.88 |
| ASTM 1692 Burn, in/min (BHA) | 1.87 | 2.14 | 1.81 | 1.83 | 2.15 | 1.33 | 2.20 | 2.64 | 1.79 |
| Butler Chimney Test | | | | | | | | | |
| Flame height, in. | >11 | >11 | 7.67 | >11 | >11 | 9.0 | >11 | >11 | 9.75 |
| Sec. to extinguish | 21 | 14 | 12 | 32 | 24 | 12 | 23 | 25 | 11.75 |
| % wt. retained | 55.4 | 64.8 | 84.4 | 49.5 | 50.9 | 84.6 | 47.8 | 51.5 | 88.8 |
| Dimensional Stability | | | | | | | | | |
| 158° F., 100% R-H | | | | | | | | | |
| 1 week ΔV | +3.6 | +7.0 | +4.6 | +7.7 | +16.7 | +5.0 | +5.6 | +10.3 | +3.7 |
| ΔW | −0.3 | −0.4 | −1.9 | −0.9 | −1.0 | −1.4 | −0.6 | −0.2 | −1.8 |
| ΔL | +2.4 | +4.6 | +3.2 | +4.7 | +10.1 | +3.4 | +3.4 | +7.1 | +3.5 |
| 4 weeks ΔV | +7.7 | +17.5 | +8.7 | +14.1 | +35.5 | +8.4 | +10.6 | +24.8 | +6.9 |
| ΔW | −0.2 | 0.0 | −2.0 | −1.3 | −2.0 | −2.0 | −0.7 | −0.7 | −2.6 |
| ΔL | +4.7 | +10.3 | +5.9 | +8.6 | +18.0 | +5.6 | +6.4 | +15.0 | +5.7 |

| | Phenol/M-300 Based (See Table II) | | | | | |
|---|---|---|---|---|---|---|
| Fire Retardant | Ex. 1 | Ex. 1 | Ex. 1 | Ex. 2 | Ex. 2 | Ex. 2 |
| Formulation, pbw | | | | | | |
| THANOL ® R-350-X² (OH = 526) | 34.6 | 22.9 | — | 34.5 | 22.8 | — |
| TERATE ® 203³ (OH = 309) | — | 15.2 | — | — | 15.1 | — |
| R-440⁴ (OH = 258) | — | — | 27.4 | — | — | 27.2 |
| R-440⁴ (OH = 252) | | | | | | |
| Fire Retardant | 4.9 | 4.9 | 4.8 | 4.9 | 4.9 | 4.7 |
| DC-193⁵ | 0.5 | 0.5 | 0.5 | 0.5 | 0.5 | 0.5 |
| R-11A⁶ | 13.0 | 13.0 | 12.0 | 13.0 | 13.0 | 12.0 |
| Water | — | 0.3 | — | — | 0.3 | — |
| FOMREZ ® UL-32⁷ | — | 0.01 | — | — | 0.01 | — |
| T-45⁸ | — | — | 1.0 | — | — | 1.0 |
| MONDUR ® MR⁹ | | | | | | |
| PAPI ® 27¹⁰ | 47.0 | 43.2 | 54.3 | 47.1 | 43.4 | 54.6 |
| Index | 1.05 | 1.05 | 3.0 | 1.05 | 1.05 | 3.0 |
| Reaction Profile | | | | | | |
| Times (sec), mixing | 15 | 12 | 6 | 15 | 12 | 6 |
| Times (sec), cream | 27 | 18 | 15 | 18 | 13 | 14 |
| Times (sec), gel | 100 | 74 | 72 | 87 | 68 | 64 |
| Times (sec), tack free | 137 | 104 | 98 | 106 | 98 | 108 |

-continued
EXPERIMENTAL FIRE RETARDANT EVALUATIONS

| | | | | | | |
|---|---|---|---|---|---|---|
| Times (sec), rise | 216 | 162 | 150 | 184 | 149 | 155 |
| Initial Surface Friability | None | None | Yes | None | None | Yes |
| Foam appearance | Good | Good | Fair | Good | Good | Good |
| Physical Properties | | | | | | |
| Density, pcf | 2.04 | 1.69 | 2.04 | 2.00 | 1.65 | 2.00 |
| K-factor | 0.111 | 0.113 | 0.114 | 0.112 | 0.113 | 0.114 |
| Compressive strength, | | | | | | |
| psi, with rise | 46.12 | 34.98 | 34.64 | 45.20 | 33.29 | 34.51 |
| against rise | 16.67 | 10.89 | 15.09 | 15.92 | 10.05 | 13.94 |
| Heat distortion, °C. | 148 | 119 | 210 | 148 | 122 | 209 |
| Closed cells, | 91.89 | 92.81 | 92.60 | 91.98 | 93.01 | 92.70 |
| Friability, % wt. loss, 10 min | 16.03 | 3.07 | 7.57 | 6.67 | 1.98 | 5.03 |
| ASTM 1692 Burn, in/min (BHA) | 2.05 | 2.41 | 1.79 | 1.87 | 2.57 | 1.75 |
| Butler Chimney Test | | | | | | |
| Flame height, in. | >11 | >11 | 10.0 | >11 | >11 | >11 |
| Sec. to extinguish | 28 | 13 | 13 | 28 | 22 | 12 |
| % wt. retained | 45.3 | 65.2 | 85.6 | 44.2 | 53.6 | 83.3 |
| Dimensional Stability | | | | | | |
| 158° F., 100% R-H | | | | | | |
| 1 week ΔV | +4.4 | +13.6 | +5.8 | +4.6 | +10.8 | +4.9 |
| ΔW | +0.2 | −0.3 | −1.8 | +0.1 | −0.4 | −1.5 |
| ΔL | +2.7 | +8.9 | +5.6 | +3.0 | +7.2 | +4.2 |
| 4 weeks ΔV | +10.1 | +34.0 | +9.4 | +11.1 | +30.0 | +8.7 |
| ΔW | +0.1 | −0.9 | −2.4 | 0.0 | −0.9 | −2.2 |
| ΔL | +5.9 | +18.7 | +8.1 | +6.7 | +17.3 | +6.6 |

[1] ANTIBLAZE ® 80 - Tris-(2-chloropropyl phosphate) fire retardant made by Mobil Chemical Co.
[2] Aromatic amino polyol sold by Texaco Chemical Co.
[3] Aromatic polyester polyol sold by Hercules, Inc.
[4] Experimental aromatic polyester polyol made by Texaco Chemical Co.
[5] Silicone surfactant sold by Dow—Corning.
[6] Trichlorofluoromethane sold by E. I. duPont de Nemours & Co.
[7] Organic tin catalyst sold by Witco Chemical Corp.
[8] Potassium octoate in glycol sold by M&T Chemical Co.
[9] Polymeric isocyanate sold by Mobay Chemical Corp.
[10] Polymeric isocyanate sold by Upjohn Co.

We claim:

1. A compound comprising a phenol which is substituted by a phosphorus containing structure having the formula:

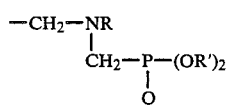

in which R is an alkanol or polyoxyalkylene group, and R' is an alkyl group, said compound being a polyol.

2. The compound of claim 1 in which the phenol is nonylphenol, phenol, isopropyl phenol, a cresol, dodecylphenol or Bisphenol A.

3. The compound of claim 1 as the product of a Mannich reaction.

4. A compound comprising a phenol which is substituted by a phosphorus containing structure having the formula:

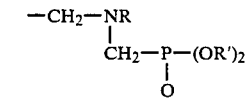

in which R is an alkanol or polyoxypropylene group, and R' is a methyl or ethyl group, said compound being a polyol.

5. The compound of claim 4 in which the phenol is nonylphenol, phenol, isopropyl phenol, a cresol, dodecylphenol or Bisphenol A.

6. The compound of claim 4 as the product of a Mannich reaction.

7. A compound having the formula:

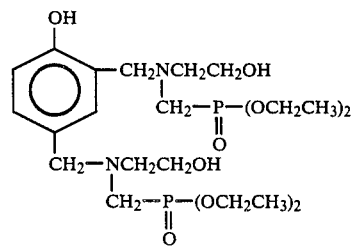

* * * * *